United States Patent [19]

Munavalli et al.

[11] Patent Number: 5,349,076

[45] Date of Patent: Sep. 20, 1994

[54] METHYL BIS(TRIFLUOROMETHYLTHIO)ARSINE

[75] Inventors: Shekar Munavalli, Bel Air; David I. Rossman, Baltimore, both of Md.

[73] Assignee: The United States of America as represented by the Secretary of the Army, Washington, D.C.

[21] Appl. No.: 146,722

[22] Filed: Sep. 17, 1993

Related U.S. Application Data

[63] Continuation of Ser. No. 961,962, Oct. 16, 1992, abandoned.

[51] Int. Cl.$^5$ ............................. C07F 9/70; C07F 1/08
[52] U.S. Cl. .................................. 556/72; 556/71; 556/76; 556/113; 568/21; 568/38
[58] Field of Search .................... 556/113, 71, 72, 76; 568/21, 38

[56] References Cited

PUBLICATIONS

Kondratenko et al., Synthesis, No. 6/7, pp. 667–669 (1985).
Man et al., J. A. C. S., vol. 81, No. 14, pp. 3575–3577 (1959).
Cullen et al., Canadian Journal of Chemistry, vol. 45, pp. 379–382 (1967).
Harris, J. Org. Chem., vol. 32, No. 7, pp. 2063–2074 (1967).

*Primary Examiner*—Jose' G. Dees
*Assistant Examiner*—Porfirio Nazario-Gonzalez
*Attorney, Agent, or Firm*—Anthony T. Lane; Edward Goldberg; Michael C. Sachs

[57] ABSTRACT

Disclosed is an improved method of preparation of trifluoromethylthiocopper in a very highly purified state and its application to the synthesis of organic and inorganic compounds containing the trifluoromethylthio moiety. Biological testing has shown that dimethyl(trifluoromethylthio)arsine is one of the most potent lung irritants known.

1 Claim, No Drawings

METHYL BIS(TRIFLUOROMETHYLTHIO)ARSINE

GOVERNMENTAL INTEREST

The invention described herein may be manufactured, used and licensed by or for the United States Government without the payment of royalties thereon.

This is a continuation, of application Ser. No. 07/961,962, filed Oct. 16, 1992, now abandoned.

FIELD OF INVENTION

Preparation and synthetic application of Trifluoromethylthiocopper.

BACKGROUND OF THE INVENTION

This invention relates to the development of an improved method of preparing trifluoromethylthiocopper in a colorless solid state, its stability and use in the synthesis of biologically and pharmacologically active organic and inorganic compounds incorporating the trifluoromethylthiyl group.

Although the chemistry of trifluoromethylthiyl group dates back to 1939 ((a) French Patent 503,920 (1939), (b) O. Scherrer, Angew. Chem., 52, 457, (1939)), interest in this functional group remained dormant until the synthesis of bis(trifluoromethyl) disulfide ((a) F. W. Bennett, G. R. A. Brandt, H. J. Emeleus and R. N. Haszeldine, Nature, 116, 225, 1950. (b) G. R. A. Brandt, H. J. Emeleus and R. N. Haszeldine, J. Chem. Soc., 2198, 1952.). Since then, bis(trifluoromethyl) disulfide has been prepared by various procedures ((a) M. Haupstschein and A. V. Grosse, J. Am. Chem. Soc., 73, 5461, 1951, (b) R. N. Haszeldine and J. M. Kidd, J. Chem. Soc., 3219, 3223, 1953. (c) E. Kober, J. Am. Chem. Soc., 81, 4810, 1959. (d) E. Mann, D. D. Coffman and E. L. Mutterties, J. Am. Chem. Soc., 81, 3575, 1959. (e) H. J. Emeleus and A. Hass, J. Chem. Soc., 1271, 1963. (f) H. Kloosterzeil, Rec. trav. Chem. (Holland), 82, 497, 1963.). In fact, it is the synthesis of bis(trifluoromethylthio)mercury from the trifluoromethylthiyl group that provided the impetus for the renewal of interest in the chemistry of trifluoromethylthiyl group ((a) G. R. A. Brandt, H. J. Emeleus and R. N. Haszeldine, J. Chem. Soc., 1298, 1952. (b) E. Mann, D. D. Coffman and E. L. Mutterties, J. Am. Chem. Soc., 81, 3575, 1959). The first report of trifluoromethylthiocopper was its in situ preparation from bis(trifluoromethylthio)mercury and copper powder ((a) W. C. Randall, P. S. Anderson, E. L. Cresson, C. A. Hunt, T. F. Lyon, K. E. Rittle, D. C. Remy, J. P. Springer, J. M. Hirsfield, K. Hoogsteen, M. Williams, E. A. Risley, and J. A. Totaro, J. Med. Chem., 22, 1222, 1979 (and references cited therein). (b) D. C. Remy, K. E. Ritchie, C. A. Hunt and M. B. Freedman, J. Org. Chem., 41, 1645, 1976. (c) D. C. Remy, K. E. Kittle, C. A. Hunt, P. S. Anderson, B. A. Arison, E. I. Engelhardt, B. V. Clineschmidt, V. J. Lotti, P. R. Bunting, R. J. Ballentine, N. L. Popp, L. Flataker, J. J. Witosiawski, and C. A. Stone, J. Med. Chem., 20, 1013, 1977. (d) R. D. Dresden in "Fluorine Chemistry Reviews," Vol. IV, P. Tarrant(Ed), Marcel Decker, Inc., New York (1969). (e) E. A. Nadiff, S. Lapschutz, P. N. Craig and M. Gordon, J. Org. Chem., 25, 60, 1960. (f) E. Mann, D. D. Coffman and E. L. Mutterties, J. Am. Chem. Soc., 81, 3575, 1959). Our own interest in the trifluoromethylthiyl group was kindled by a report that this functionality significantly altered the pharmacological properties of the parent compound and endowed it with antipsychotic properties (D. C. Remy, K. E. Kittle, C. A. Hunt, P. S. Anderson, B. A. Arison, E. I. Engelhardt, B. V. Clineschmidt, V. J. Lotti, P. R. Bunting, R. J. Ballentine, N. L. Popp, L. Flataker, J. J. Witoslawski, and C. A. Stone, J. Med. Chem., 20, 1013, 1977). Thus the introduction of trifluoromethylthiyl moiety in the 3-position of cycloheptadienes enhanced their pharmacological properties and binding to molecular receptors (D. C. Remy, K. E. Kittle, C. A. Hunt, P. S. Anderson, B. A. Arison, E. I. Engelhardt, B. V. Clineschmidt, V. J. Lotti, P. R. Bunting, R. J. Ballentine, N. L. Popp, L. Flataker, J. J. Witoslawski, and C. A. Stone, J. Med. Chem., 20, 1013, 1977). Additional biological properties have been attributed to the trifluoromethylthiyl group (R. D. Dresden in "Fluorine Chemistry Reviews," vol. IV, P. Tarrant-(Ed), Marcel Decker, Inc., New York (1969). (e) E. A. Nadiff, S. Lapschutz, P. N. Craign and M. Gordon, J. Org. Chem., 25, 60, 1960). The trifluoromethylthiyl group has, for the same reason, been incorporated into various novel heterocyclic systems ((a) M. R. C. Gerstenberger, A. Haas and F. Liebig, J. Fluorine Chem., 25, 60, 1960. (b) D. M. Mulvey and H. Jones, J. Heterocyclic Chem., 12, 597, 1975). In connection with other on-going projects in or laboratory, large quantities of trifluoromethylthiocopper were required. After several unsuccessful attempts to prepare trifluoromethylthiocopper according to the published procedure (N. V. Kondratecnko, A. A. Kolomeytsev, V. I. Popov and L. M. Yagupolskii, Synthesis 667, 1985), we explored several solvents such as diethyl ether, diisopropyl ether and tetrahydrofuran. Realizing that solvents having high dielectric constants are better suited to form a complex with trifluoromethylthiocopper and that it may precipitate out by itself from a concentrated solution, we then attempted to prepare trifluoromethylthiocopper as a complex of acetonitrile. Our expectation was rewarded.

SUMMARY OF INVENTION

Generally stated, the present invention provides an improved method of preparing trifluoromethylthiocopper by reacting freshly distilled dry acetonitrile, activated copper powder (dried overnight under vacuum) and bis(trifluoromethyl) disulfide at 50°–60° C. for 14–16 hours under argon. A decided advantage of this improved procedure is the formation of a colorless crystalline complex, which can be filtered under argon and dried under vacuum at 55°–60° C. for 24 hours to give a colorless powder. The reagent thus prepared can be stored at ambient temperature, under anhydrous conditions for several months without significant loss of activity. The solid, according to GC/MS data is a 1:1 complex of trifluoromethylthiocopper and acetonitrile. Unlike bis(trifluoromethylthio)mercury, which is extremely air sensitive and highly hygroscopic, trifluoromethylthiocopper may be weighed in air without loss of activity.

DETAILED DESCRIPTION OF THE INVENTION, SYNTHESIS AND USE OF TRIFLUOROMETHYLTHIOCOPPER

The procedure of this invention is specifically applicable to the introduction of the trifluoromeththio function into organic and inorganic compounds using trifluoromethylthiocopper: acetonitrile complex as described herein.

Warning: Because of the high toxicity associated with bis(trifluoromethyl)disulfide, extreme care should be exercised in working with this compound. The mass spectra were recorded on a Finnigan Model 5100 GC.MS equipped with a silica 25 m×0.31 mm (i.d) SE-54 capillary column (J&W Scientific, Rancho Cordova, Calif.). Routine GC separations were accomplished with a Hewlett-Packard Model 5890A gas chromatograph equipped with a 30 m×0.53 mm (i.d.) column (J&W Scientific, Folsom Calif.). The reactions were carried out in a flame-dried, argon purged three-neck flask equipped with a dry ice/acetone cooled trap. The temperature of the coolant circulating through the condenser was maintained at −20° C. Air sensitive reagents were weighed under argon in a glove bag. The products formed after the termination of the reaction were flash-distilled under reduced pressure and the products trapped in receivers cooled to −78° C. The distillate was subjected to fractional distillation under vacuum and analyzed by GC and GC/MS.

DETAILED DESCRIPTION OF THE PROCESS

Reactions of trifluoromethylthiocopper with halomethanes and arsenicals are given as examples.

TRIFLUOROMETHYLTHIOCOPPER

Freshly distilled dry acetonitrile (50 ml) and freshly activated copper powder (7.6 g, 0.13 gram-atoms) were placed in a flame-dried, argon purged 100 mL three-neck flask equipped with gas inlet tube, reflux condenser attached to a dry ice/acetone cooled condenser with an argon gas/vacuum inlet. After cooling the reaction flask to −78° C., the system was evacuated to 90 mm and bis(trifluoromethyl) disulfide (16 g, 0.08 moles) was sparged into the stirred flask containing dry activated copper powder. After stirring at −78° C. for ½ hour, the reaction mixture was allowed to warm to ambient temperature and then heated at 55°–60° C. for 14–16 hours. During the course of the reaction the copper metal dissolved to give a clear solution. The reaction solution was concentrated under an argon atmosphere and the concentrate refrigerated overnight to give 12 g of a white crystalline solid. Overnight drying under vacuum gave a product which was shown to be a 1:1 trifluoromethylthiocopper: acetonitrile adduct (GC/MS), m.p. 184°–186° C. (decomp.). Stored at ambient temperature under anhydrous conditions, the material is stable for several months without significant loss of activity.

TABLE 1

| Mass Spectral Fragmentation of CF$_3$SCu: CH$_3$CN | | | |
|---|---|---|---|
| m/e | Fragments | m/e | Fragments |
| 102 | CF$_3$SH | 41 | CH$_3$CN |
| 82 | CSF$_2$ | 40 | CH$_2$CN |
| 69 | CF$_3$ | 39 | CHCN |
| 63 | CSF | 38 | CCN |
| 44 | SC | 33 | SH |
| 42 | CH$_3$CNH | | |

EXAMPLE 1

Bis(trifluoromethylthio)methane: A mixture of trifluoromethylthiocopper (2.0 g, 0.01 moles), dry distilled diiodomethane (1.33 g, 0.005 moles) and dry sulfolane was heated under nitrogen at 85°–90° C. for 18 hours. The reaction mixture was cooled, flash-distilled under reduced pressure and the distillate collected in a dry ice/acetone cooled trap. The GC analysis of the distillate showed it to be composed of acetonitrile (coming from the copper adduct), the desired product (r.t.=4.3 min.) trifluoromethylthioiodomethane (r.t.=9.4 min.) and diiodomethane (r.t.=12.2 min.). Fractional distillation through a Vigreux column gave a pure sample (J. F. Harris J. Org. Chem., 32, 2063, 1967). $^1$H NMR: δ4.28 (s, —CH$_2$—). $^{-C}$ NMR: δ129.9 (SCF$_3$); and δ28.6 (CH$_2$). MS: M+(216); 147(M-CF$_3$); 115(M-SCF$_3$); 101(SCF$_3$); 82(CSF$_2$); 69(CF$_3$); 63(CSF); 50(CF$_2$); and 45 (CSH).

EXAMPLE 2

Bis(trifluoromethyl)trisulfide: To an ice-cold slurry of trifluoromethylthioicopper (6.3 g, 0.03 moles) in dry xylene (5 mL), a solution or sulfur dichloride (3.09 g, 0.03 moles) in dry xylene (3 ml) was added dropwise under nitrogen with stirring. The reaction mixture was stirred at ambient temperature for 30–45 minutes, flash distilled under reduced pressure and the distillate collected in a dry ice/acetone cooled receiver. Fractional distillation of the distillate through a Vigreux column gave a pure sample of the desired product (r.t.=5.1 min.) R. N. Haszeldine and J. M. Kidd, J. Chem. Soc., 3219, 3223, 1953. The residue contained small amounts of tetra- and pentasulfides. NMR: $^{13}$C: δ128.7 (q) (J=314±1 HZ; $^{19}$F δ44.5 (s). MS: M+(234:215(M-F); 165(M-CF$_3$): 133(M-SCF$_3$); 101(SCF$_3$); 96(SSS); 82(CSF$_2$); 69(CF$_3$); 64(SS); and 50(CF$_2$).

EXAMPLE 3

Tris(trifluoromethylthio)methane: A mixture of iodoform (3.94 g, 0.01 mole) trifluoromethylthiocopper (6.0 g, 0.03 mole) in freshly distilled dry acetonitrile (10 mL) was heated at 100°–105° C. (bath temperature) under nitrogen with stirring for 24 hours. The reaction mixture was cooled to room temperature, and flash distilled under reduced pressure. The distillate was collected into a received cooled to −78° C. The distillate was redistilled to give tris(trifluoromethylthio)methane [2.3 g, b.p. 104.5–105.5° C., Lit. 106.5° C. J. F. Harris J. Org. Chem., 32, 2063, 1967]. Gas chromatographic analysis showed the absence of impurities. The product had a r.t. of 4.6 min. $^1$H NMR: δ5.93 (s); $^{13}$C NMR; δ128 (SCF$_3$ and δ46.8 (CH). MS: M+(316); 247(M-CF$_3$); 215(M-SCF$_3$); 82(CSF$_2$); 76(CS$_2$) and 69(CF$_3$).

EXAMPLE 4

Trifluoromethylthioacetonitrile: To trifluoromethylthiocopper (4.1 g, 0.02 mole) in freshly distilled dry acetonitrile (10 ml) was added with stirring and under nitrogen a solution of bromoacetonitrile (2.4 g, 0.02 mole) in dry acetonitrile (5 ml). The mixture was heated at 85° C. for 18 hours and then at 95° C. for 4 hours. It was then cooled to room temperature and flash distilled at 90 mm. The distillate was collected into a receiver cooled at 78° C. Fractional distillation using a Vigreux column gave trifluoromethylthioacetonitrile 1.3 g. b.p. 57-5°–58° C.; (Lit. 59° C.; J. F. Harris J. Org. Chem., 27, 1340, 1972). Gas chromatographic analysis indicated the r.t. to be 8.1 min. This compound had been prepared in three steps starting from trifluoromethylsulfenyl chloride and ketene (J. F. Harris J. Org. Chem., 27, 1340, 1972). The identity of the product was further confirmed by its mass spectral data. MS: M+(141); 122(M-F); 101(SCF$_3$); 82(CSF$_2$); 69(CF$_3$); 63(CSF); 46OCSH$_2$); and 40(CH$_2$CN).

EXAMPLE 5

Dimethyl(trifluoromethylthio)arsine: (a) A mixture of dimethyl bromoarsine (5.0 g, 0.027 mole) and bis(trifluoromethylthio) mercury (6.03 g, 0.018 mole) was heated for 5 hours at 85°–90° C. in the absence of light. The reaction mixture was cooled to room temperature and flash distilled under reduced pressure. The distillate was collected into a receiver cooled to −78° C. Gas chromatographic analysis showed to distillate to consist of 68% of the desired product and 28% of the starting material accompanied by trace impurities containing dimethyl fluoroarsine, dimethyl chloroarsine, and thiocarbonyl fluoride. When the reaction temperature was raised to 90°–100° C., additional impurities such as bis(-trifluoromethyl)disulfide, trifluoromethylthiocarbonyl fluoride, bis(trifluoromethyl)trithiocarbonate and bis(-trifluoromethylthio)methyl arsine were detected by GC/MS. The last compound must have arisen from methyl dibromoarsine present as an impurity in the starting material or else from a "thermal equilibrium." The identity of the desired product was confirmed by its mass spectral data. The flash distillate was fractionally distilled to give the desired product (98.5% pure by GC, r.t.=8.5 min.). MS: $M^+(206)$; $191(M—CH_3)$; $187(M—F)$; $176(AsSCF_3)$; $145(AsSF_2)$; $137(M—CF_3)$; $122(CH_3AsS)$; $109(CH_3AsF)$; $105(M—SCF_3)$; $94(AsF)$; $89(AsCH_2)$; $82(CSF_2)$; $75(As)$; $69(CF_3)$; $63(CSF)$; and $45(CSH)$ (b) Similar results were obtained when a mixture containing stoichiometric quantities of dimethyl bromoarsine (1.85 g, 0.01 mole) (Johnson Mathey, 152 Andover Street, Danvers, Mass. 01923) and trifluoromethylthiocopper (2.05 g, 0.01 mole) was heated at 80°–90° C. under nitrogen for 8 hours in the absence of light. The reaction mixture was cooled to ambient temperature, flash distilled under reduced pressure and the distillate collected into a receiver cooled to −78° C. Gas chromatographic analysis showed the r.t. to be 8.5 min. The GC/MS data was identical to that described above. Animal inhalation studies of this compound have demonstrated it to be one of the most potent lung irritant known to date.

EXAMPLE 6

Methyl bis(trifluoromethylthio) arsine:

(a) A mixture of dichloromethylarsine (3.12 g, 0.02 mole) and bis(trifluoromethylthio)mercury (8.06 g, 0.02 mole) was heated with stirring under nitrogen in an oil bath at 75°–85° C. for 4 hours. The mixture was cooled to room temperature, flash distilled under reduced pressure and the distillate collected into a receiver cooled to −78° C. The yield and r.t. were 3.5 g. and 11.8 min. respectively. GC/MS confirmed its identity. MS: $M^+(292)$; $273(M—F)$; $191(M—SCF_3)$; $176(AsSCF_3)$; $141(CH_3AsSF)$; $121(CH_2AsS)$; $107(AsS)$; $89(AsCH_2)$; $69(CF_3)$ and $63(CSF)$.

(b) A mixture of methyl dichloroarsine (0.01 mole) and trifluoromethylthiocopper (0.02 mole) in dry sulfolane (5 ml) was heated with stirring at 90°–100° C. under argon for 5 hours. The reaction mixture was cooled and processed as before in example 6a to give 1.6 g. of the expected product. This compound was identical (G.C. and GC/MS) with that prepared as described above.

What is claimed is:

1. Methyl bis(trifluoromethylthio)arsine.

* * * * *